United States Patent [19]

Shields

[11] Patent Number: 5,007,901

[45] Date of Patent: Apr. 16, 1991

[54] INTRAVENOUS CATHETER INSERTION DEVICE

[76] Inventor: Jack W. Shields, 1950 Las Tunas Rd., Santa Barbara, Calif. 93103

[21] Appl. No.: 582,128

[22] Filed: Sep. 12, 1990

Related U.S. Application Data

[63] Continuation of Ser. No. 440,859, Nov. 24, 1989, abandoned.

[51] Int. Cl.$^5$ .............................................. A61M 5/50
[52] U.S. Cl. .................... 604/110; 604/164; 604/195
[58] Field of Search ............................ 604/164-170, 604/110, 192, 195, 198, 263, 158, 197, 171

[56] References Cited

U.S. PATENT DOCUMENTS

| | | | |
|---|---|---|---|
| 3,595,230 | 7/1971 | Suyeoka et al. | 604/164 |
| 3,820,652 | 6/1974 | Thackston | 604/110 X |
| 4,177,809 | 12/1979 | Moorehead | 604/167 X |
| 4,592,744 | 6/1986 | Jagger et al. | 604/192 |
| 4,652,256 | 3/1987 | Vaillancourt | 604/52 |
| 4,747,831 | 5/1988 | Kulli | 604/110 |
| 4,781,692 | 11/1988 | Jagger et al. | 604/164 |
| 4,790,822 | 12/1988 | Haining | 604/110 |
| 4,808,169 | 2/1989 | Haber et al. | 604/195 |
| 4,826,484 | 5/1989 | Haber et al. | 604/110 |
| 4,832,696 | 5/1989 | Luther et al. | 604/164 |
| 4,834,718 | 5/1989 | McDonald | 604/195 |
| 4,846,805 | 7/1989 | Sitar | 604/165 |
| 4,850,961 | 7/1989 | Wanderer et al. | 604/53 |
| 4,917,669 | 4/1990 | Bonaldo | 604/164 |
| 4,919,652 | 4/1990 | Alter et al. | 604/110 |

FOREIGN PATENT DOCUMENTS

WO89/00432  1/1989  PCT Int'l Appl. .................. 604/110

*Primary Examiner*—John D. Yasko
*Assistant Examiner*—Adam J. Cermak
*Attorney, Agent, or Firm*—Michael G. Petit

[57] ABSTRACT

An intravenous catheter insertion device comprising an intravenous silastic or Teflon catheter, a hollow-bore steel introducer needle, a break-away needle guide and a needle trap. Prior to catheter insertion the needle is concentric within the catheter with one end extending past the distal end of the catheter. The other end of the needle is releasably attached to a needle guide. After the needle is used to guide the catheter into a vein, the needle guide is withdrawn. As the needle guide is withdrawn, the introducer-needle is drawn out of the intravenous catheter into the needle trap. As the needle guide is further withdrawn, the introducer-needle breaks loose from the needle guide to remain safely housed within the trap. The invention is easily adapted for use with most conventional intravenous catheter assemblies.

4 Claims, 2 Drawing Sheets

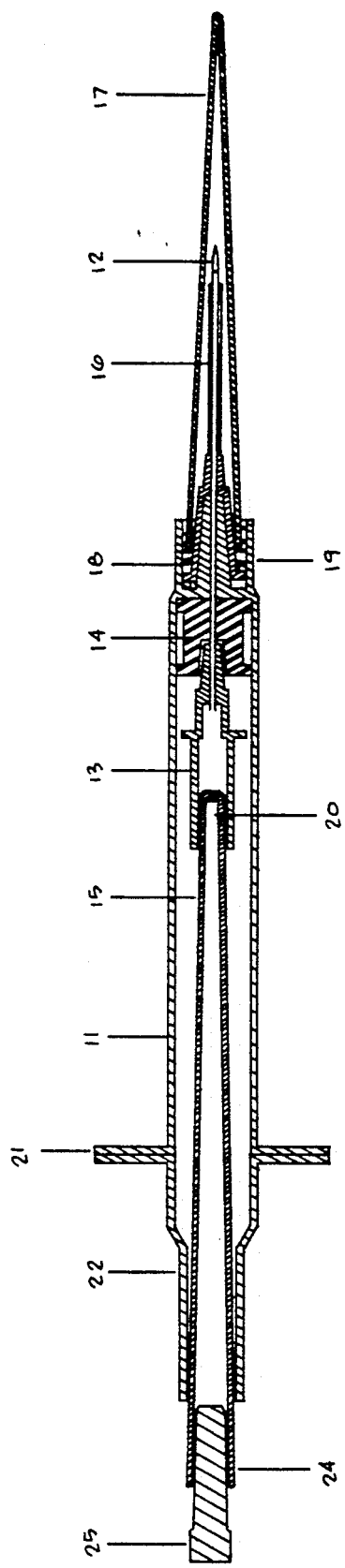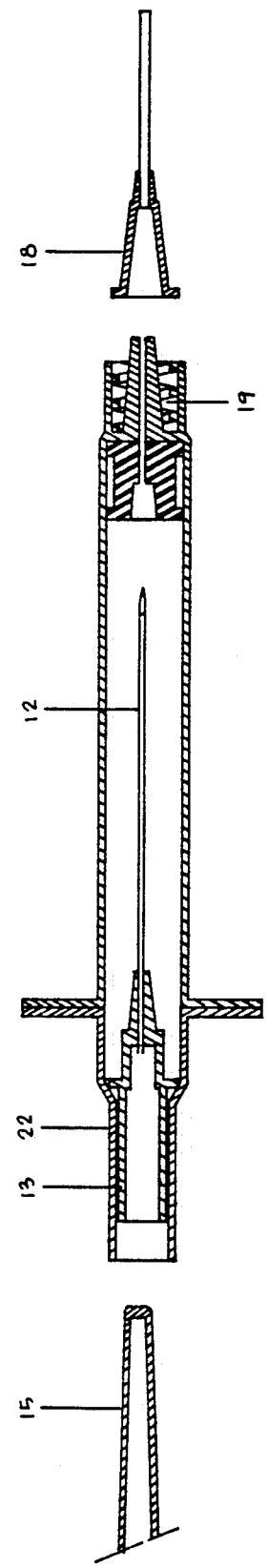
FIG. 1
FIG. 2

INTRAVENOUS CATHETER INSERTION DEVICE

This is a continuation of application Ser. No. 07/440,859, filed Nov. 24, 1989 now abandoned.

BACKGROUND OF THE INVENTION

1. Field of the Invention

Intravenous catheter insertion device which protects the user from accidental needle-stick injury from the insertion needle and the patient from Teflon or Silastic embolism.

2. Prior Art

"Needle-stick" injuries, especially with the hollow-bore steel needles commonly used for withdrawing blood are now the most common cause of AIDS and serum hepatitis in health care workers who are otherwise at low risk. Such needles, once used, may contain a large number of blood cells. The U.S. Centers for Disease Control have advised workers not to manually resheath needles used for giving injections or withdrawing blood, and have urged the deposition of used needles into safe containers as soon as possible. (See MMWR June 23, 1989/Vol. 38/No. 5–6—Guidelines for prevention of transmission of Human Immunodeficiency Virus and Hepatitis V Virus to Health-Care and Public-Safety Workers).

Each kind of needle used for withdrawing blood, giving infusions into veins or giving medications under the skin presents special safety problems. For intravenous needles such as phlebotomy needles, "butterfly needles", vacutainer needles and some straight needle/syringe combinations, these problems have been addressed. In a co-pending U.S. patent application Ser. No. 07/226,134, now U.S. Pat. No. 4,932,946, the present inventor describes a hub-mounted permanently attached slit elastic sheath designed for protecting the user, as well as the patient from accidental needle stick injury. Here I describe methods for preventing needle-stick injuries from hollow bore steel needles used to insert silastic intravenous catheters, especially after such introducing needles are withdrawn from the soft hub-mounted catheters.

The use of syrettes to insert the contents of cartridges containing medications, especially penicillin, morphine or cocaine derivatives, through retractable, disposable needles has been commonly practiced since World War II. Such hinging metal holder/cartridge/retractable needle assemblies are still useful for giving shots with minimal chance for the health care workers getting "needle-stuck" after use. However, removal of the exhausted cartridges and disposable needles from reusable housing assemblies for subsequent disposal expose personnel to the danger of accidental needle stick injury from the dangerous and, possibly, HIV or HBV-contaminated hollow-bore needle tips.

In U.S. Pat. No. 4,334,536 issued Jun. 15, 1982, Pfeger described pre-filled syringes in which the means for attaching the needle assembly to the syringe, the needle cover and the activating mechanism are unitized, but breakable at specific points to expose the needle and empty the syringe. However, Pfleger provides no means for safely resheathing the needle after use.

Haber et al, U.S. Pat. No. 4,767,413 issued Aug. 30, 1988 describes a disposable dental syrette which manually retracts and safely resheaths the needle back in the housing after the cartridge contents have been injected into soft tissues. Such syrettes are considered to be user-safe with respect to needle-stick injuries, but are not suitable for giving continuous, prolonged infusions into soft tissues or into veins.

Beck, in U.S. Pat. No. 4,068,660 issued Jan. 17, 1978 describes disposable assemblies for safely inserting break-away silastic catheters via straight or curved hollow-bore steel needles into veins for the purpose of giving continuous infusions. Beck describes methods to prevent the sharp insertion needles from shearing the catheters. However, no means were described for safely resheathing the hollow-bore steel needles obliged to contain blood after proximal withdrawal from the catheter via a firmly attached wire needle guide.

In U.S. Pat. No. 4,702,735 issued Oct. 27, 1985, Luther, Snyder and Whitehouse describe an assembly consisting of a break-away needle and catheter operable by the user employing only one hand. The device included adhesive-coated taped wings to enhance in-site attachment of the silastic catheter for long term use. As in the other prior art references, no means were described for safely sheathing the broken-away steel needle after insertion of the silastic catheter; or for securing the catheter firmly to the assembly during insertion.

In U.S. Pat. No. 4,642,101 issued Feb. 10, 1987, Krolikowski and Shahnarian described a smooth bulbous tipped catheter which, after withdrawal of the inserting steel needle, leaves a blunt non-lacerating conduit for intravenous fluid. The catheter was designed with a broad base to prevent breakage, and with multiple break-away perforated tabs to provide options for suturing the hub to patient's skin. No means were described for safely resheathing the steel needle used to insert the device.

Sitar, in U.S. Pat. No. 4,846,805, discloses a catheter insertion device comprising a long cylindrical collection tube having a distal conical catheter subassembly slides on the conical end to substantially cover the introducer needle. Once the introducer needle penetrates a selected vein and the catheter is advanced into the lumen of the vein, a guard member which is concentrically and slideably mounted over the collection tube is slid forward pushing the catheter off of the conical end of the introducer tube. At the end of its travel, the guard mechanically locks in place to protectively cover the entire introducer needle. Sitar's device has the disadvantage that although the intravenous catheter is prevented from rotating over the introducer needle, the catheter can inadvertently slip forward such that it may be sheared by the needle. Moreover, once the introducer needle is withdrawn from the catheter, the catheter can immediately spill venous blood over the patient.

In addition to the problem of accidental needle stick injury inherent in the prior art devices, there is an additional risk of silastic embolism to the patient. If the tip of the introducer needle is permitted to slide back inside the silastic intravenous catheter, there is a danger that the sharp tip may remove a portion of the inner wall of the catheter. The removed piece may enter the blood stream and cause embolism.

Currently, an untold number of related devices are under development. These may include concentric plastic tubes which slide back over steel needles used for one-handed insertion of hub-mounted silastic catheters (such as PROTECTIV ™ manufactured by CRITIKON); or tubes into which the steel needles can be retracted. None of these embody means for securely anchoring the detachable silastic catheter during intravenous insertion; for varying the length of exposed steel needle beyond the tip of the silastic catheter; for preventing the embolization of cut-off silastic in the case of inaccurate insertion; or for leaving the catheter insertion needle in a safe disposable needle trap. It should be understood that the observation of "flash-back" of venous blood during needle insertion will be enhanced by usage of parts of optimal optic clarity.

SUMMARY

A tubular concentric assembly such as a luer lock syringe is used as a handle for the insertion of a standard hub-mounted silastic catheter by means of a hollow-bore steel introducer needle. After placement of the catheter, the introducer needle is manually retracted from the catheter assembly by means of a needle guide. Once retracted, the needle becomes trapped therein as the needle guide separates from the introducer needle by means of a breakable proximal attachment between the introducer needle and its retractable guide.

The above-described invention is simple. It comprises a needle trap, a catheter, an introducer needle and a break-away needle guide, one end of which extends beyond a needle trap to be grasped by the fingers. The other end of the needle guide is breakably attached to the introducer needle. The introducer needle is used to guide the intravenous catheter into a vein in a manner well known in the art.

One object of the invention is to provide an intravenous catheter insertion assembly which prevents "needle-stick injury" by the introducer needle after the catheter has been placed, especially in emergency situations, operating rooms, in mobile units and housekeeping facilities where safe containers for needle disposal are not always handy.

Another object of the invention is to provide an intravenous catheter insertion assembly which is easy to use and inexpensive to fabricate.

By providing a luer-locked anchor for the silastic catheter and an elastic means of advancing the steel needle $+/-1$ mm. through the catheter, the accuracy of needle placement is enhanced; while the likelihood of embolization of silastic from the catheter is greatly reduced. It is, therefore, still another object of the invention to provide an intravenous catheter insertion assembly which is easy to use and reduces the risk of embolism due to fragmentation of the catheter by the insertion needle.

BRIEF DESCRIPTION OF THE DRAWINGS

FIG. 1 is a longitudinal cross-sectional representation of a disposably sheathed intravenous catheter assembly showing the steel insertion needle slightly advanced beyond the leading end of the catheter.

FIG. 2 is a fragmented cross-sectional view of the needle trap portion of the assembly of FIG. 1 showing the needle holder and hollow-bore steel needle locked within the needle trap.

DESCRIPTION OF THE PREFERRED EMBODIMENTS

Figure 5:
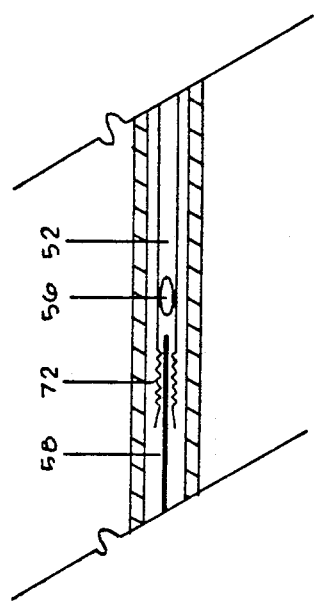
FIG. 5 is a magnified cross-sectional view of the breakaway portion of the catheter assembly of FIG. 3 showing the frictional coupling between the needle and needle guide.

A first preferred embodiment of the present invention is shown in FIG. 1. The needle trap, which also serves as a handle for the insertion of a catheter, consists of a standard luer-lock syringe barrel (11) containing a needle guide (15) which is roughly the size and shape of a tuberculin syringe and which has a male tapered end (20) onto which a standard hollow-bore steel insertion needle (12) and its transparent polyvinyl needle holder (13) are matingly connected by either friction or luer-lock coupling. The hollow-bore steel insertion needle is stabilized within the needle trap by means of a standard rubber plug (14) through which the needle passes as it exits the assembly to pass through the intravenous catheter (16) to extend beyond the tip of the soft catheter; and by frictional attachment of the needle holder to the hollow needle guide (15). The exterior portion of the needle (12) is sheathed by a silastic catheter (16) beyond which the sharp tip of the needle extends. Sterility of the needle and catheter are protected by a throw-away puncture-proof scabbard (17).

The trailing or proximal end of the intravenous catheter (16) is fitted to the needle trap by means of a standard needle hub (18) which screws into a luer-lock fitting (19) on the needle trap. A tapered concentric tube of decreasing bore (22) is bonded to the proximal or trailing end of the needle trap (11) or to a flange integral therewith (21) s that the body of the needle guide (15) will slide through the narrowest bore of the tapered tube (22), but the needle holder (13) will not (see FIG. 2). A compatible female fitting (24) of appropriate diameter is molded into the proximal or trailing end of the hollow needle guide for filling the assembly with infusion fluid or withdrawing venous blood, if so desired. This hub is normally occluded by a removable male cap (25) held firmly by friction means into the female fitting.

After the catheter/needle assembly is inserted into a vein (not shown), as evidenced by "flash-back" of venous blood from the hollow-bore steel needle into its clear vinyl holder (13), and the breakaway needle guide (15) is withdrawn the needle and its holder become stuck within the tapered portion (22) of the needle trap by friction. The needle guide may then be separated from the needle holder by pulling. After removal of the needle guide, the distal catheter (16) may then be detached and left in place by grasping its proximal luer-lock hub (18) while twisting the needle trap assembly counterclockwise and removing it from the catheter.

As shown in FIG. 2, when the clear needle holder is fully retracted, friction between the rigid plastic needle holder (13) and a softer tapered inner surface of the needle trap (22) will prevent sliding of the insertion needle in either direction. Removal of the break-away needle guide (15) is accomplished by means of either traction or traction and twisting. Once the needle guide breaks away from the needle holder, the needle holder and needle are safely contained within the needle trap for disposal. The rubber plug (14) in addition to stabilizing the needle during insertion, also serves to block exit of the sharp needle from the trap if the needle holder becomes unstuck from the tapered part of the trap.

Figure 3:
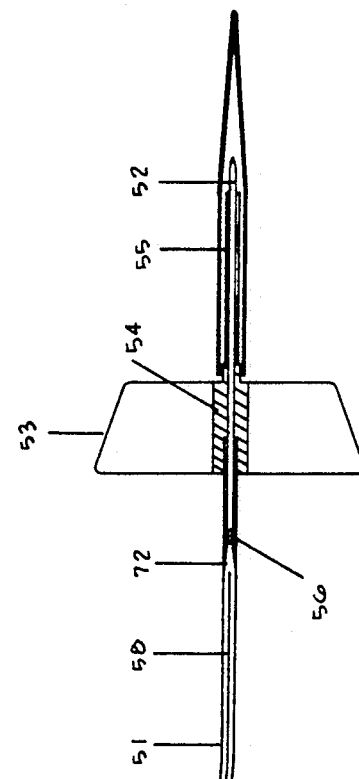
FIG. 3 is a longitudinal cross-sectional representation of a sheathed butterfly or "winged" needle assembly with a retractable break-away guide wire.
Figure 3:
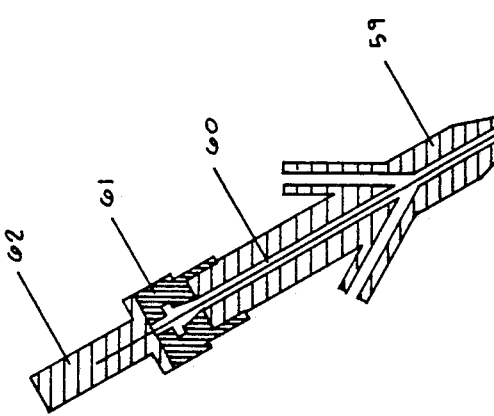

For those who prefer to use butterfly infusion sets permanently linked to silastic catheters, a second preferred embodiment using a breakable wire linkage for the insertion needle is shown in FIG. 3. A "winged" or "butterfly" catheter hub is substituted for the standard round needle hub ((18) FIG. 1). The "butterfly" configuration of the silastic catheter hub supplies increased surface for holding, after the catheter is placed in the vein and the user retracts the steel needle into its trap; and provides a broader surface for taping the inserted catheter to a patient's skin (not shown). The butterfly wings may be set in a gliding plane in relation to the long axis of the needle in order to facilitate needle insertion, as well as to keep the proximal end of the hub from indenting the skin over a selected vein after the silastic catheter is secured by taping. Such assemblies (see, for example, U.S. Pat. No. 4,177,809 to Moorehead) characteristically use tiny intraluminal guide wires as a needle guide to control the position of the sharp needle tip in relation to the leading end of the silastic catheter tube. The user safety of such assemblies can be augmented by making these wires breakable so that the steel insertion needles can be safely housed in a proximally located needle trap, as shown.

This second preferred embodiment of the present invention is particularly adapted for butterfly infusion sets consisting of a silastic tube (51) through which a specially made hollow bore steel needle (52) slides to insert the silastic catheter. During insertion, the needle is held steady by the body and attached wings of the molded butterfly (53) through which the needle point extends to the exterior. The body of the butterfly also forms the permanent hub (54) which holds the base of an intravenous silastic catheter (55). The steel needle, essential for insertion of the catheter, is perforated (56) along its shaft near the trailing end to permit "flashback" of visible blood when the needle and surrounding silastic catheter are inserted into a vein. Proximal to this perforation, the needle is crimped (57) and proximally splayed around a stainless steel wire (58) used to hold the needle in place and to withdraw the needle into a tripartite proximal hub assembly (59) after intravenous insertion of the catheter. The central portion of the tripartite proximal hub (60) forms a rigid tube aligned with the long axis of the steel needle. The length of this tube, added to the depth of the affixed trap, directly in line with the long axis of the needle. The needle trap must be longer than the steel needle. At its proximal end, this needle trap portion of the assembly is covered with an air-tight rubber stopper (74) through which the guide wire is manipulated by a rigid handle (62). Before insertion of the needle into a vein, the wire normally holds the sharp tip extended just beyond the distal opening of the silastic catheter. After the catheter is properly positioned within the vein, the rigid handle (62) provides means for withdrawing the insertion needle back into a locked position within the needle trap (see FIG. 4). The remaining sections of the tripartite hub are inlet ports for injecting fluid into the system, preferably via a standard male adapter on one side, and a rubber stopper on the other (not shown).

It should be added that the first preferred embodiment can be made as a winged or "butterfly" assembly by attaching flexible wings to the flanged catheter hub in order to increase surface area for grasping the taping (not shown).

Figure 4:
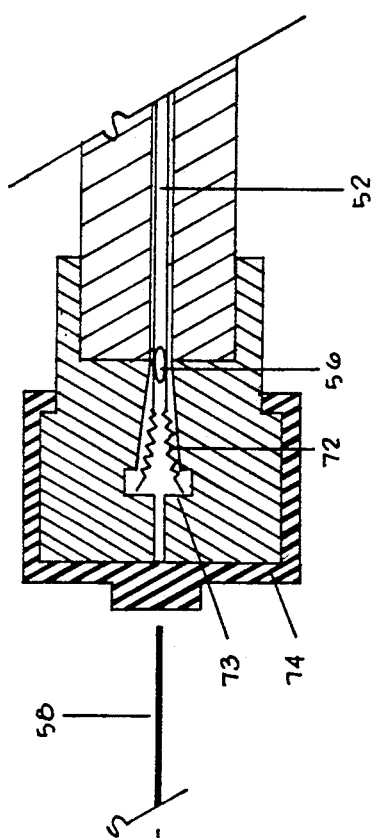
FIG. 4 is a magnified cross-sectional view of the needle trap portion of FIG. 3 showing the trailing end of the needle within the trap after breaking away from the needle guide.

After the winged silastic catheter is in place, the insertion needle is withdrawn in the direction of the arrow (FIG. 4). FIG. 4 shows a detail of the proximal hub portion after the guide wire is withdrawn from the winged needle assembly. Comparison with FIG. 5 will reveal that mechanical splaying of the proximal portion of the hollow needle in the defined stepped pattern serves to release the needle from the needle guide.

The needle (52) becomes safely housed in the needle trap and central portion of the proximal hub (59), and is prevented from leaving by a splaying of crimped parts (72) by an internal wedge-like part (73) within the bore of the affixed trap (see FIGS. 4 and 5 for details). Such splaying, in turn, releases the crimp on the trailing end of the steel needle, such that the needle remains behind; while the insertion wire and its handle are retracted in the direction of the arrow. Although a dulled tip on the wire may have blood on its surface, after being wiped on its passage back through the rubber cap (74) it will be much less likely to inflict a dangerous wound than a rapier-like needle with blood in its bore, thrusting unpredictably on the end of a similar wire no longer confined within combinations of rigid and elastic tubing.

In the first preferred embodiment, the use of a luer-lock syringe as both the needle trap and a means for holding the device during catheter insertion offers the following advantages:

1. Use of a luer-lock syringe for both a needle trap and for holding the silastic catheter makes it relatively easy for the user to accurately insert the sheathed needle into a vein, because the assembly puts syringe/needle in customary positions and the catheter is prevented from sliding off the trap if the insertion needle is pulled back.

2. Because the rubber needle stabilizer plug permits the needle to easily slide through during retraction, very little negative pressure will be generated in the syringe. In fact, if the needle stabilizer plug is tightly fitted to the internal bore of the syringe, it is unlikely to move during retraction of the needle guide. Thus, the needle stabilizer plug will provide an additional barrier through which a retracted needle must pass before getting back out of the syringe and appended trap.

3. Because no suction or significant increase in positive pressure will be generated before the hollow bore steel needle is withdrawn from a vein via traction on the needle guide, it is optional whether the system is filled with infusion fluid or left filled with air before venepuncture.

4. Finally, the combined use of a flanged hub and a luer-lock syringe for silastic catheter introduction increases user control over the position of the catheter and decreases the likelihood of silastic (usually Teflon) embolization in the patient. Cutting off of the silastic by twisting of the needle bevel or advancement of the catheter over the needle cannot occur unless the user intentionally pulls the needle guide back some distance and then advances it.

It should be noted that trapping the used introducer needle to prevent accidental needle-stick injury is an essential part of the invention. Moreover, the use of a breakaway coupling provides an assembly that is more convenient to use.

While the foregoing intravenous catheter insertion assembly has been described, in part, in terms of specific embodiments, these embodiments are exemplary only and not intended to be limiting. It will be appreciated by those skilled in the art that wide variation in details can be made without departing from the spirit of the invention as hereinafter claimed.

What I claim is:

1. An integral intravenous catheter placement assembly for introducing a catheter into the vein of a patient comprising, in combination, an intravenous catheter and an intravenous catheter insertion assembly,. said intravenous catheter having a distal end adapted for insertion within a vein of a patient, said catheter further having a proximal end having a luer-lock hub attached thereto, said luer-lock hub providing means for the secure attachment of said intravenous catheter to said intravenous catheter insertion assembly, said intravenous catheter insertion assembly further comprising a needle trap with a luer-lock fitting on its distal end to releasably engage said proximal hub on said intravenous catheter, a hollow introducer needle having a proximal end and a sharp distal end, said introducer needle being disposed within the lumen of said intravenous catheter, and a needle guide breakably attached to the proximal end of said hollow introducer needle.

2. The improved intravenous catheter assembly of claim 1 wherein said needle trap further comprises a hollow puncture-proof tubular container disposed within the assembly to share a common axis with said catheter into which container said hollow introducer needle is manually retracted and becomes trapped after said hollow steel introducer needle is completely withdrawn from said catheter by means of said needle guide.

3. An improved intravenous catheter placement assembly for introducing a catheter into the vein of a patient comprising:
 (a) a catheter having a hubbed leading end and a trailing end;
 (b) a catheter introducer needle having a sharpened leading end and a trailing end;
 (c) a substantially linear needle guide having a leading end breakably attached to the trailing end of said catheter introducer needle;
 (d) a hollow needle trap having a leading end and a trailing end, said trap leading end having means thereon for removable attachment to the trailing end of said catheter, and said trap trailing end having an opening therein permitting passage of said needle guide therethrough, and said trap trailing end having means therein for preventing said introducer needle from being pulled through said opening in said trailing end of said needle trap by said needle guide.

4. The improved intravenous catheter placement assembly of claim 3 wherein said means for preventing said introducer needle from being pulled through said opening in said trailing end of said needle trap comprises a needle holder with at least one dimension sufficiently large to prevent passage of said needle holder through said opening.

* * * * *